June 15, 1976
J. C. MIKKELSEN
BEGONIA PLANT
Filed May 7, 1975
Plant Pat. 3,911
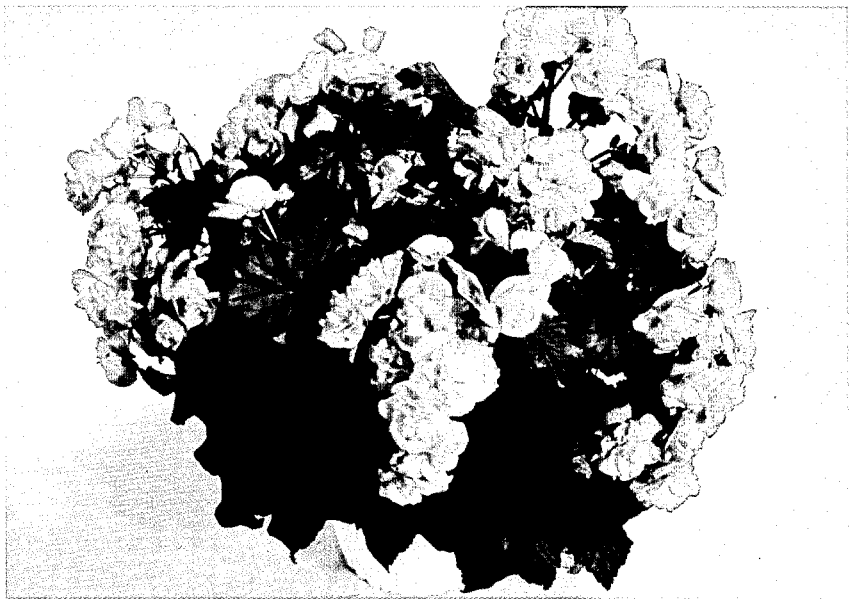

United States Patent

Plant Pat. 3,911

Patented June 15, 1976

3,911

BEGONIA PLANT

James C. Mikkelsen, Ashtabula, Ohio, assignor to Mikkelsens Inc., Ashtabula, Ohio Filed May 7, 1975, Ser. No. 575,440

Int. Cl. A01h *5/00*

U.S. Cl. Plt.—68 1 Claim

The present invention relates to a new and distinctive variety of begonia plant known by the cultivar name Fantasy and bontanically known as *Begonia elatior* (*hiemalis*—Fotsch), discovered by me as a mutation of a peach colored double flowering begonia plant identified by code 8104 that has never been commercially utilized in any way. The parent cultivar (#8104) was a mutation from Aphrodite Rose, an unpatented cultivar. Asexual reproduction by stem and leaf cuttings has reproduced the unique features of the new cultivar through successive propagations.

The following characteristics distinguish the new begonia from both its parent and other begonias commercially known and used in the floriculture industry:

(1) Compared to the peach colored flowers of the parent variety #8104 the color of the flowers of Fantasy is a much darker, deeper shade of rose red.

(2) The growth habit of Fantasy is upright rather than procumbent as in the parent variety. Growth is more compact than either Schwabenland or Aphrodite types.

(3) The keeping quality of the flowers of Fantasy in the home is two to three times as great as that of the commercially well known Rieger Aphrodite cultivars.

(4) Observed from a distance so that individual leaves cannot be distinguished. Fantasy appears very much like an azalea.

(5) The flowers are 5–6 cm. in diameter, double and displayed in rather tight clusters.

(6) Unlike most of the double flowering Rieger Aphrodite types propagated by stem cuttings, Fantasy propagates best by leaf cuttings, producing adventitious shoots at the base of the leaf petiole as in the Rieger Schwabenland types of begonias. This character in propagation results in better quality plants for the growers producing the finished plant. Leaf propagation time is 10 to 14 days longer than for leaf cuttings of Schwabenland Red, disclosed in U.S. Plant Pat. No. 3,320.

(7) In nearly two years of testing Fantasy in areas of plants infested with common powdery mildew, the new cultivar would be classified as being immune to this fungus disease. Fantasy shows more resistance to the bacterial disease *Xanthomonas begoniae* than does the previously patented Rieger begonias. This is of significant importance to commercial growers.

(8) The upright growth characteristic of Fantasy is of the utmost value. However, Fantasy can with proper growing techniques be produced in hanging baskets, but it is not as graceful as Rieger Aphrodites for this purpose or use.

(9) Fantasy encompasses the upright growth of Schwabenland Red, the double flowers of Aphrodite Rose, (unpatented) the propagation characteristics of Schwabenland types and the greater disease resistance of the Aphrodite types. Adding to these characteristics a unique displaying of flowers resembling the azalea, and having greatly improved keeping qualities in the home, Fantasy opens up new and greater production opportunities of flowering pot plant begonias for U.S. growers.

The accompanying colored photograph illustrates the overall appearance of the new cultivar taken as a face view of the plant and showing the colors as true as it is reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

Parentage: A mutation of a non-commercialized elatior begonia identified by code number 8104.

Propagation: By leaf cuttings that root in approximately 35 days and further develop adventitious buds at the base of the leaf petiole in an additional approximately 45 days in the summer to approximately 75 days in low light conditions of winter in Ashtabula, Ohio. Propagation can also be done by vegetative top or stem cuttings. Better control of flowering response is obtained by leaf cutting propagation.

Rooting habit: Rooting is considered to be slower than for Schwabenland types, but quite profuse, fine, and dendritic.

Plant form: Upright, bushy.

Habit of growth: Compact, close internodes, self-branching.

Blooming habits: Free flowering, clustered double blooms, produced over a long period of time interrupted basically by adverse environmental conditions of high light intensity high temperatures and more than 12 hours of day length.

Blooming season: Would normally be classified as a winter flowering begonia. Modern propagation and culture techniques permits this cultivar to be produced as a flowering plant all year around.

Foliage: Is of above average quantity because of close internodes and considerable self-branching.

Size: Mature leaves under normal cultural practices in Ohio are approximately 10 cm. wide by 10 cm. long, short petioles.

Shape: Nearly round, flat, very little cupping.

Texture: Smooth, waxy, rigid, thick.

Margin: Very small serrations—nearly complete.

Color: Young foliage, upper—near 146A; lower—areas between veins reddish brown. Mature foliage—upper—darker than 139A; lower—dark, dull, red—veins extremely protruding.

Disease resistance: Apparently immune to powdery mildew, highly resistant to *Xanthomonas begoniae*.

FLOWERS

Borne: On a compound cyme, clustered because of confinement by the abundance of foliage and because the flower stems do not seem to elongate above the leaf canopy.

Quantity: Above average since there is considerable self-branching to allow for more flowering areas.

Buds: Are flat and approximately 8 to 10 mm. in diameter before opening. Flowers approaching maturity measure 5 to 6 cm. in diameter.

Tepals: Are rose red between 50A and 51B.

Reproductive organs: None found to date.

I claim:

1. A new and distinct cultivar of begonia plant characterized particularly as to uniqueness by the combined characteristics of upright growth habit; rose red tepal color; superior keeping quality; double flower form; propagatable from leaf as well as stem cuttings, and by its apparent immunity to common powdery mildew and high resistance to *Xanthomonas begoniae*.

No references cited.

ROBERT E. BAGWILL, Primary Examiner